(12) United States Patent
Whitehead et al.

(10) Patent No.: US 11,046,960 B2
(45) Date of Patent: Jun. 29, 2021

(54) LIGAND BINDING ASSAY FOR DETECTING GIBBERELLINS

(71) Applicant: University of Johannesburg, Johannesburg (ZA)

(72) Inventors: Charles Stephen Whitehead, Johannesburg (ZA); Eduard Venter, Pretoria (ZA); Joseph Adrian Walker, Pretoria (ZA); Kha Quan Tram, Ontario (CA)

(73) Assignee: University of Johannesburg, Johannesburg (ZA)

(*) Notice: Subject to any disclaimer, the term of this patent is extended or adjusted under 35 U.S.C. 154(b) by 211 days.

(21) Appl. No.: 16/320,934

(22) PCT Filed: Jul. 26, 2017

(86) PCT No.: PCT/IB2017/054544
§ 371 (c)(1),
(2) Date: Jan. 25, 2019

(87) PCT Pub. No.: WO2018/020442
PCT Pub. Date: Feb. 1, 2018

(65) Prior Publication Data
US 2020/0378967 A1  Dec. 3, 2020

(30) Foreign Application Priority Data

Jul. 26, 2016 (ZA) .................................. 2016/05194
Dec. 12, 2016 (ZA) .................................. 2016/08528

(51) Int. Cl.
*C12N 15/115* (2010.01)
*G01N 33/53* (2006.01)
(Continued)

(52) U.S. Cl.
CPC .......... *C12N 15/115* (2013.01); *C12Q 1/6818* (2013.01); *G01N 21/55* (2013.01);
(Continued)

(58) Field of Classification Search
CPC .............. C12N 15/115; C12N 2310/16; C12N 2320/10; C12Q 1/6818; G01N 33/53;
(Continued)

(56) References Cited

FOREIGN PATENT DOCUMENTS

| CN | 103454245 B | 4/2016 |
|---|---|---|
| CN | 103674935 B | 5/2016 |

(Continued)

OTHER PUBLICATIONS

MacMillan (J. Plant Growth Regul., 2002, 20:387-442) (Year: 2002).*

(Continued)

*Primary Examiner* — Jeremy C Flinders
(74) *Attorney, Agent, or Firm* — Knobbe Martens Olson & Bear LLP

(57) ABSTRACT

A method of detecting gibberellins, for example in barley. Current methods of detecting gibberellins require dedicated equipment which makes it expensive and time consuming. A ligand bind assay for detecting gibberellins in which the above disadvantages could at least partially be overcome or alleviated is described. The ligand binding assay uses aptamers for the detection of gibberellins in barley seeds.

14 Claims, 9 Drawing Sheets
Specification includes a Sequence Listing.

(51) Int. Cl.
  *G01N 33/74* (2006.01)
  *C12Q 1/6818* (2018.01)
  *G01N 21/55* (2014.01)
  *G01N 33/566* (2006.01)

(52) U.S. Cl.
  CPC ............ *G01N 33/53* (2013.01); *G01N 33/566* (2013.01); *G01N 33/74* (2013.01); *C12N 2310/16* (2013.01); *C12N 2320/10* (2013.01); *G01N 2021/558* (2013.01); *G01N 2333/415* (2013.01); *G01N 2500/02* (2013.01)

(58) Field of Classification Search
  CPC ................. G01N 33/566; G01N 33/74; G01N 2021/558; G01N 2333/415; G01N 2500/02
  See application file for complete search history.

(56) References Cited

FOREIGN PATENT DOCUMENTS

| | | |
|---|---|---|
| EP | 0692537 A2 | 1/1996 |
| EP | 1873239 A1 | 1/2008 |
| EP | 2907878 A1 | 8/2015 |

OTHER PUBLICATIONS

Grozio et al., "Selection and Characterization of Single Stranded DNA Aptamers for the Hormone Abscisic Acid", Nucleic Acid Therapeutics, vol . 23, No. 5, Oct. 1, 2013 (Oct. 1, 2013), pp. 322-331, XP055433680, us ISSN: 2159-3337, DOI: 10.1089/nat.2013.0418.

Huntley R P et al., "Cytokinins and gibberellins in sap exudate of the oil palm", Phytochemi, Pergamon Press, GB, vol. 60, No. 2, May 1, 2002 (May 1, 2002), pp. 117-127, XP004353805, ISSN: 0031-9422, DOI: 10.1016/S0031-9422(02)00099-7.

Smith et al., "An Immunological Approach to Gibberellin Purification and Quantification", Plant Physiol, Jan. 1, 1989 (Jan. 1, 1989), pp. 1148-1155, XP055433678, Retrieved from the Internet: URL:https://www.ncbi.nlm.nih.gov/pmc/articles/PMC1061857/pdf/pIntphys00642-0380.pdf.

Su et al., "Simul taneous determination of zeatin and systemin by coupling graphene oxide-protected aptamers with catalytic recycling of DNase", Sensors and Actuators B: Chemical: International Journal Devoted to Research and Development of Physical and Chemical Transducers, Elsevier BV, NL, vol. 230, Feb. 22, 2016 (Feb. 22, 2016), pp. 442-448, XP029506795, ISSN: 0925-4005, DOI: 10.1016/J.SNB.2016.02.087.

Ueguchi-Tanaka et al., "Molecular Interactions of a Soluble Gibberellin Receptor, GID1, with a Rice DELLA Protein", SLR1, and Gibberellin 11, The Plant Cell Online, vol. 19, No. 7, Jul. 13, 2007 (Jul. 13, 2007), pp. 2140-2155, XP055110357, ISSN: 1040-4651, DOI: 10.1105/tpc.106.043729 t.

International Search Report issued in application No. PCT/IB2017/054544, dated Dec. 13, 2017.

* cited by examiner

| Rank | | | |
|---|---|---|---|
| Cycle 20 | Cycle 18 | Cycle 16 | Sequence |
| 1 | 4 | 8 | SEQ ID NO. 1 |
| 2 | 1 | 2 | SEQ ID NO. 2 |
| 3 | 2 | 1 | SEQ ID NO. 3 |
| 4 | 9 | 14 | SEQ ID NO. 4 |
| 5 | 3 | 2 | SEQ ID NO. 5 |
| 6 | 4 | -- | SEQ ID NO. 6 |
| 7 | 17 | 13 | SEQ ID NO. 7 |
| 8 | 19 | -- | SEQ ID NO. 8 |
| 9 | 6 | -- | SEQ ID NO. 9 |
| 10 | 19 | -- | SEQ ID NO. 10 |

| Rank | | | |
|---|---|---|---|
| Cycle 20 | Cycle 18 | Cycle 16 | Sequence |
| 1 | 1 | 2 | SEQ ID NO. 2 |
| 2 | 4 | 11 | SEQ ID NO. 1 |
| 3 | 3 | 1 | SEQ ID NO. 3 |
| 4 | 11 | 17 | SEQ ID NO. 4 |
| 5 | 2 | 3 | SEQ ID NO. 5 |
| 6 | 8 | - | SEQ ID NO. 6 |
| 7 | 6 | 9 | SEQ ID NO. 7 |
| 8 | - | 4 | SEQ ID NO. 8 |
| 9 | 15 | 19 | SEQ ID NO. 10 |
| 10 | 31 | 13 | SEQ ID NO. 11 |
FIGURE 3
FIGURE 4
FIGURE 5

(A)

(B)

(C)

| Group | Sequence |
|---|---|
| G1 | SEQ ID NO. 2 |
| G2 | SEQ ID NO. 1 |
| G3 | SEQ ID NO. 3 |
| G4 | SEQ ID NO. 4 |
| G5 | SEQ ID NO. 5 |
| G6 | SEQ ID NO. 6 |
| G7 | SEQ ID NO. 7 |
| G8 | SEQ ID NO. 8 |
| G9 | SEQ ID NO. 10 |
| G10 | SEQ ID NO. 11 |

LIGAND BINDING ASSAY FOR DETECTING GIBBERELLINS

RELATED APPLICATIONS

This application is the U.S. National Phase under 35 U.S.C. § 371 of International Application PCT/IB2017/054544, filed Jul. 26, 2017, designating the U.S., and published in English as WO 2018/020442 on Feb. 1, 2018, which claims priority to South African Patent Application No. 2016/05194, filed Jul. 26, 2016; and South African Patent Application No. 2016/08528, filed Dec. 12, 2016 the entire contents of which are incorporated herein by reference.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the SequenceListing.txt, created Jan. 25, 2019, which is 3.28 kb bytes in size.

FIELD OF THE INVENTION

The invention relates to a ligand binding assay and more specifically, but not exclusively, to a ligand binding assay for detecting gibberellins in barley.

BACKGROUND TO THE INVENTION

Gibberellins or gibberellic acids (GAs) are plant hormones that regulate growth and influence various developmental processes, including stem elongation, germination, dormancy, flowering, sex expression, enzyme induction, and leaf and fruit senescence.

All known gibberellins are tetracyclic diterpene acids that are synthesized by the terpenoid pathway in plastids and then modified in the endoplasmic reticulum and cytosol until they reach their biologically-active form. All gibberellins are derived via the ent-gibberellane skeleton, but are synthesised via ent-kaurene.

A problem in the art is that the test to detect gibberellins requires dedicated equipment which makes it expensive and time consuming.

OBJECT OF THE INVENTION

It is accordingly an object of this invention to provide a ligand binding assay for detecting gibberellins which, at least partially alleviates the problem associated with the prior art.

SUMMARY OF THE INVENTION

In accordance with a first aspect of the invention there is provided a ligand binding assay for detecting the presence of gibberellins in a sample comprising:
a target binding element selected to bind to gibberellins; and
the target binding element being associated with a visual indicator, such that the visual indicator indicates the presence of gibberellins in the sample when the target binding element binds to gibberellins.

The gibberellins are gibberellic acids $GA_1$, $GA_3$, $GA_4$ or $GA_7$.

The target binding element is a target moiety. The moiety is an aptamer.

The aptamer has 62 nucleotides with the nucleic acid sequence (SEQ ID NO: 12)
5'-NHMCVNNNHDGCTGAGGTATGCNNNHWNDYDDNDNNHHHNHNVVHNN

NNNDNNDBNHNNNHD-3', wherein Y is T or C;
wherein M is A or C;
wherein W is A or T
wherein B is G or C or T;
wherein D is A or G or T;
wherein H is A or C or T;
wherein V is A or G or C;
wherein N is A or G or C or T, unknown, or other;
or its compliment, or an RNA equivalent of the molecule or its complement.

The aptamer has 62 nucleotides with the nucleic acid sequence (SEQ ID NO: 13)
5'-TGAGGDVNVNGCTGAGGTATGCMAAYDHMHNVNNNNNHNNNNNNNNN

NNNNNNNNNNNDHNNN-3' wherein Y is T or C;
wherein M is A or C;
wherein D is A or G or T;
wherein H is A or C or T;
wherein V is A or G or C;
wherein N is A or G or C or T, unknown, or other;
or its compliment, or an RNA equivalent of the molecule or its complement.

The aptamer may comprise a nucleic acid sequence having at least 90% homology to sequence selected from a group G1-G10 consisting of the following nucleic acid sequences selected from a group consisting of SEQ ID NO 1-11, or its compliment, or an RNA equivalent of the molecule or its complement.

The ligand binding assay may be a lateral or vertical flow assay wherein the aptamers are bound to a carrier and the indicator is provided in the form of a binding signal from saturation of aptamer binding sites on the carrier.

The lateral or vertical flow assay may be an inhibition assay.

The carrier may be gold nanoparticles and the gold nanoparticles may be bound to the aptamer by thiolation.

The surface plasma resonance from a highly localized concentration of gold nanoparticles results in a visual indicator in the absence of gibberellins in the sample. The visual indicator may be perceivable as a visible red signal on an indication portion of the lateral or vertical flow assay.

The depletion of the binding signal from saturation of aptamer binding sites on the gold nanoparticles result in the absence of the red signal in the presence of gibberellins in the sample.

The visible red signal is a result of the aptamer bound gold nanoparticle complex saturating binding sites on the carrier and thus preventing the aggregation of the gold particles.

The ligand binding assay may be in the form of a lateral flow or vertical flow disposable test with the product applied to a membrane of the disposable test.

The vertical flow disposable test may be a standard sandwich vertical flow assay or a competitive vertical flow assay.

The ligand binding assay may be a non-radioactive ligand binding assay which includes aptamers which are chemically linked to a fluorophore and quencher pair such that the visual indicator is provided in the form of fluorescence in the presence of gibberellins.

The fluorophore and quencher pair may be a nucleic acid dye and fluorescent hybridization probe.

The ligand binding assay includes aptamers which are chemically linked to an acceptor and donor pair such that the visual indicator is provided in the form of fluorescence in the presence of gibberellins.

BRIEF DESCRIPTION OF THE ACCOMPANYING DIAGRAMS

An embodiment of the invention is described below, by way of a non-limiting example only, and with reference to the accompanying drawings in which:

FIG. 3 is a table depicting the aptamer sequences form FIG. 2 aligned with each other and characterized into a pool based on 90% sequence homology;

FIG. 4 is a schematic representation of possible aptamer sequences with the class referred to as "TGAGG";

FIG. 5 is a schematic representation of possible aptamer sequences with the class referred to as "CCACC";

DETAILED DESCRIPTION OF THE INVENTION

Germination of Barley

Figures 1, 2:
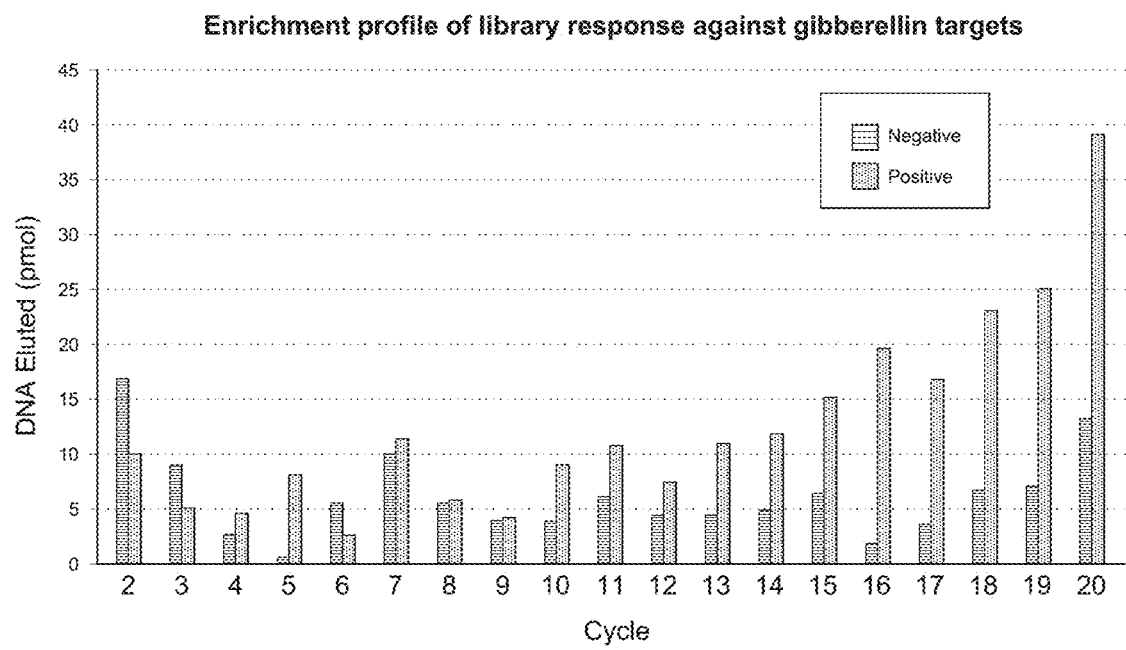
FIG. 1 is a graph illustrating the enrichment profile of the library's response against gibberellin targets.
FIG. 2 is a table depicting the most abundant aptamer sequences obtained after twenty cycles of systematic evolution of ligands by exponential enrichment (SELEX)

Barley seeds are living plant organs and their development can, for the sake of convenience, be divided into three phases, viz. growth, maturation and germination. However, it is not possible to clearly identify the transition from one phase to the next, since considerable overlap exists between the major processes characteristic of each phase and the next phase may commence before the previous phase is completed. The first two phases can only be completed while the seed is still attached to the plant. Although the initial germination processes required for final germination are initiated on the plant during the later stages of maturation, final germination usually only occurs after the seed has detached from the plant. In order for germination to succeed, seeds must have reached that stage of maturity (harvest maturity/ripeness) that will allow it to germinate fully once it is detached from the plant. After harvest, barley seeds are quiescent (dormant) until environmental conditions are favorable for germination. Germination will only occur successfully if seeds are fully imbibed. Imbibition initiates the germination processes in the seed. Imbibition of dry seeds is regarded as the critical period in germination. Stress induced by very rapid imbibition can have a negative effect on the germination of dry seeds. Seeds that are fully imbibed but then allowed to dry out again will also not germinate successfully.

This phenomenon is referred to as pre-germination. Pre-germination reduces the viability of stored dry seed because it involves partial imbibition of seed that triggers a final germination response but cannot sustain the process, or because it involves hormonal changes that initiate final germination at a stage in the development of the seed before it has finally reached harvest maturity/ripeness. In both cases some of the stored reserves and storage messenger RNA in the seed are consumed, which leaves the seed with insufficient resources to withstand prolonged storage conditions. The result is barley that germinates prematurely and which cannot be used in the malting process. It is not possible to visually inspect the seeds to determine whether pre-germination has occurred.

Gibberellins and Germination

The interaction between phytohormones, particularly between gibberellins (GAs) and abscisic acid (ABA), is an important factor controlling the transition from embryogenesis to germination in seed. During germination of barley grains, the embryo secretes GA to the aleurone layer, where it promotes the synthesis of several hydrolytic enzymes that are involved in the mobilization of starch reserves to sustain the growing embryo. Synthesis of these enzymes are blocked by ABA during seed development, in dormant seeds, and in seedlings under unfavorable germination conditions. Germination of barley seed after storage is severely suppressed by pre-germination, a condition characterized by premature seed germination while still in the ear, also known as 'pre-harvest sprouting'. This phenomenon is most often caused by prolonged exposure of mature unharvested seed to wet weather. Such a premature onset of the processes associated with germination may have an unfavorable effect on the balance between ABA and GA and in that way, suppress germination after storage. Pre-germination could stress the seed so that the concentration of ABA increases concomitant with a decrease in the pre-storage concentration of GA to unfavorable levels.

Barley seeds need to germinate in order to be used in the malting process. Seeds that do not germinate do not have sufficient germination energy (GE) and can therefore not be used in the malting process. It is therefore important to determine whether barley seeds contain the required GE. A correlation between gibberellins and GE is shown by treatment of barley seeds with an inhibitor of GA synthesis which resulted in severe inhibition of germination. The results indicated that GA-synthesis plays an important role in barley germination. Measurement of gibberellins can therefore indicate whether barley seeds have reached germination or not.

Gibberellins Detection

Detecting gibberellins requires dedicated equipment which makes it expensive and time consuming. Typically, a sample is taken from a batch and sent to a laboratory for testing by means of ELISA (enzyme-linked immunosorbent assay). ELISA testing relies on the binding of antibodies. A fairly common problem associated with the use of rapid polyclonal antibodies generated against low molecular weight compounds such as gibberellins are the low affinity of such antibody for free gibberellins. Affinity for the carrier protein compound conjugate used for immunization is generally poor in terms of detecting only the compound as the free compound is not sufficiently immunogenic as a stand-alone hapten. Therefore, antibodies are not capable of rapidly binding to the small epitope that is gibberellins. ELISA also requires several hours of incubation and a qualified technician to carry out the assay. By the time a result is obtained from a laboratory, it is possible, depending on the storage conditions, that the GE of the batch of seeds have changed.

Aptamers offer a viable alternative to antibodies and may overcome the constraints encountered when using antibodies for the detection of gibberellins. There are three types of aptamers: DNA, RNA, and peptide aptamers. All have very similar properties but are distinctly unique. It is theoretically possible for aptamers to be used against any molecular target. Aptamers bind with high specificity, precision and affinity to their specific targets. Because aptamers structurally conform to bind to their targets, this gives aptamers a wider range of possible targets when compared with antibodies, which require antigens and epitopes along with an immune response for their targets.

In Vitro Selection of Aptamers

In accordance with the above a ligand binding assay for detecting the presence of gibberellins in a sample was developed. The assay comprises a target binding element selected to bind to gibberellins. The target binding element is associated with a visual indicator and the visual indicator indicates the presence of gibberellins in the sample when the target binding element binds to gibberellins. The gibberellins may be gibberellic acids $GA_1$, $GA_3$, $GA_4$ or $GA_7$ and the target binding element may be a target moiety in the form of an aptamer.

In vitro selection of the aptamers were carried out by screening free gibberellins against a proprietary aptamer library. A bead-based systematic evolution of ligands by exponential enrichment (SELEX) approach was used. Aptamers with a binding affinity towards $GA_1$, $GA_3$, $GA_4$ and $GA_7$ were identified. All four targets were mixed into one solution to a final concentration of 1 mM each. As mentioned earlier, gibberellins are plant hormones synthesized from diterpenoid acids via terpenoid pathway to yield tetracyclic diterpene acids. These bioactive molecules are involved in various aspects of plant development, however, of interest to this project, their detection is important for monitoring germination. Of all known gibberellins, $GA_1$, $GA_3$, $GA_4$, and $GA_7$ are the most bioactive, hence their use as targets for in vitro selection.

The in vitro selection of the aptamers against the four gibberellins were performed over 20 cycles of the bead-based SELEX approach and is depicted in FIG. 1. Typical in vitro selection experiments tend to conclude within 10-15 cycles, however, 20 cycles were performed for this project due to slow enrichment of aptamer molecules. The first indication for successful aptamer isolation was seen at the end of cycle 12 as the rate of DNA eluted from the solid support in the presence of gibberellins exceeded the rate of DNA eluted in the absence of gibberellins. At the end of cycle 12, the library was submitted for deep sequencing analysis. However, sequencing data suggested that enrichment of desired sequences has only begun and no clear dominance of one particular sequence was observed. As a result, in vitro selection was resumed for an additional 8 cycles. By the end of cycle 20, there was a clear enrichment profile of the library's response against gibberellin targets as shown in FIG. 1. This library was then submitted for deep sequencing analysis.

Deep Sequencing Analysis

Illumina® MiSeq was used for deep sequence analysis to analyze cycles 14, 16, 18, and 20. By doing multiple sequencing analysis over several progressive cycles, the library can be monitored for sequences with varying degrees of enrichment. In addition, the behaviors of the top 10 most abundant sequences can be tracked throughout the selection cycle. Analysis of sequencing data begins by looking at the frequency of specific sequences within the library. In vitro selection is a form of competition between sequence molecules, whereby the most responsive sequence is selectively enriched while poor or inactive sequences are discarded. The more frequent (or abundant) a sequence is seen would suggest that these molecules would have some form of favorable activity towards the gibberellin targets.

FIG. 2 shows the sequences ranked in order of abundance at the end of cycle 20 of enrichment. In the second and third column of the table, the respective sequences are tracked to see where they were ranked in cycles 18 and cycle 16. This type of analysis may be able to depict the growth or depreciation of molecules as they compete against other molecules over many cycles of selection. For example, sequence ranked 3 and 5 were highly ranked in the earlier cycles of in vitro selection, however, by the $20^{th}$ cycle, their population has declined as more potent sequences begin to multiply. Sequence rank 1 is an example of high growth rates. In cycle 16, it was ranked $8^{th}$ among the population, however, after only two cycles (cycle 18) it became the fourth most dominant population and then became the most dominant in the final cycle. This is a desired pattern and can be indicative of an active aptamer.

FIG. 3 shows all the ranked sequences are then aligned with each other and categorized into a pool based on 90% sequence similarity. Once pooled, the same analysis can be performed to determine the rate of enrichment or deterioration of a particular class over the course of selection. In this set of data, the first ranked class is the second most abundant sequence (SEQ ID NO. 2) found in FIG. 2, while the most abundant sequence (SEQ ID NO. 1) in FIG. 2 was ranked second with respect to classification. There are two notable trends that may be important for determining aptamer activity. The first is the fast rate at which the second ranked class has progressed over cycles 16 to 20. Second, most of the sequences and classes begin with a specific sequence pattern of "TGAGG".

Structural Analysis

FIGS. 4 and 5 are schematic representations produced to further analyze the top-ranking "CCACC" class and the "TGAGG" class respectively. (Schematic representation was generated from the following reference: 1) Crooks G E, Hon G, Chandonia J M, Brenner S E WebLogo: *A sequence logo generator, Genome Research*, 14:1188-1190, (2004) 2) Schneider T D, Stephens R M. 1990. *Sequence Logos: A New Way to Display Consensus Sequences. Nucleic Acids*

Res. 18:6097-6100). The "CCACC" class may be generalized as an aptamer molecule of 62 nucleotides with nucleic acid sequence 5'-NHMCVNNNHDGCT-GAGGTATGCNNNHWNDYDD-NDNNHHHNHNVVHNNNNNDNNDBN HNNNHD-3' (SEQ ID NO. 12), wherein Y is T or C, M is A or C, W is A or T, B is G or C or T, D is A or G or T, H is A or C or T, V is A or G or C and N is A or G or C or T. Similarly, the "TGAGG" class may be generalized as an aptamer molecule of 62 nucleotides with nucleic acid sequence 5'-TGAGGDVNVNGCTGAGGTATGC-MAAYDHMHNVNNNNNHNNNNNNNNNNNNNNN NNN NDHNNN-3' (SEQ ID NO. 13) wherein Y is T or C, M is A or C, D is A or G or T, H is A or C or T, V is A or G or C and N is A or G or C or T. The generalized sequences or its compliment, or an RNA equivalent of the molecule may also be effective.

The "TGAGG" was a highly-conserved sequence and was readily found within the sequencing library. In fact, the "TGAGG" was repeated twice in each sequence, with the second being found at the capture site.

The "CCACC" sequence class was not as apparent as the "TGAGG" family of sequences. There were certain positions that indicate sites of conservation.

Structure of the Sequence Representatives

Figure 6:
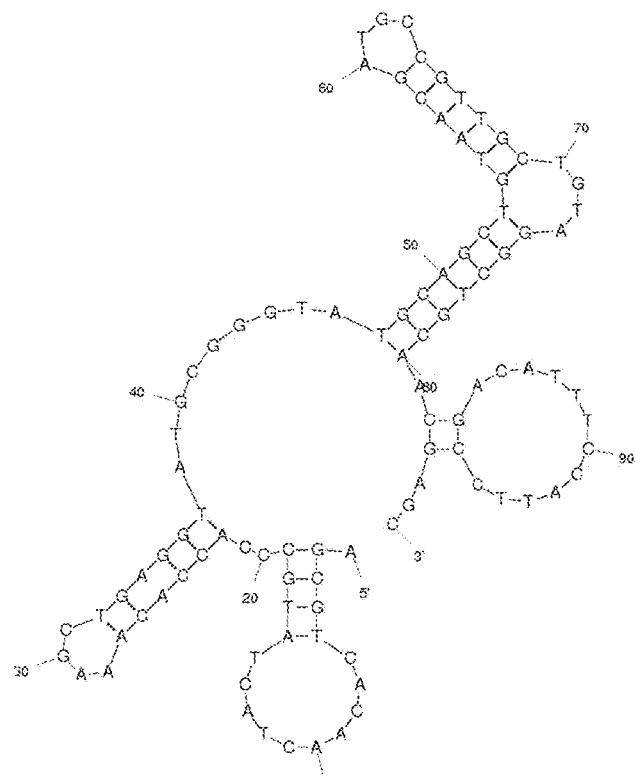
FIG. 6 is a schematic presentation of a possible structure of the sequence representative from class "TGAGG" in its most stable form.
Figure 6:
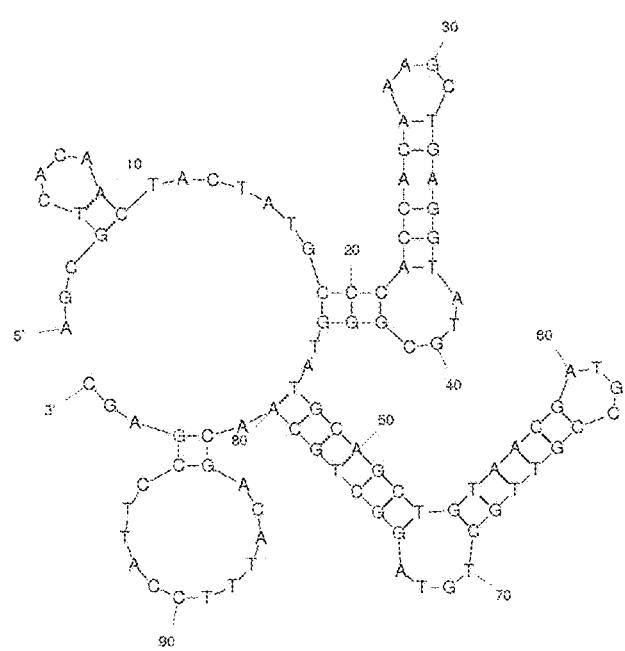
Figure 6:
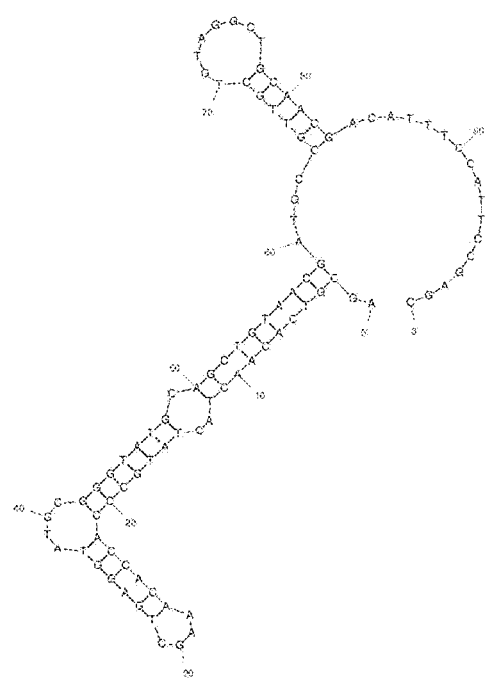
Figure 7:
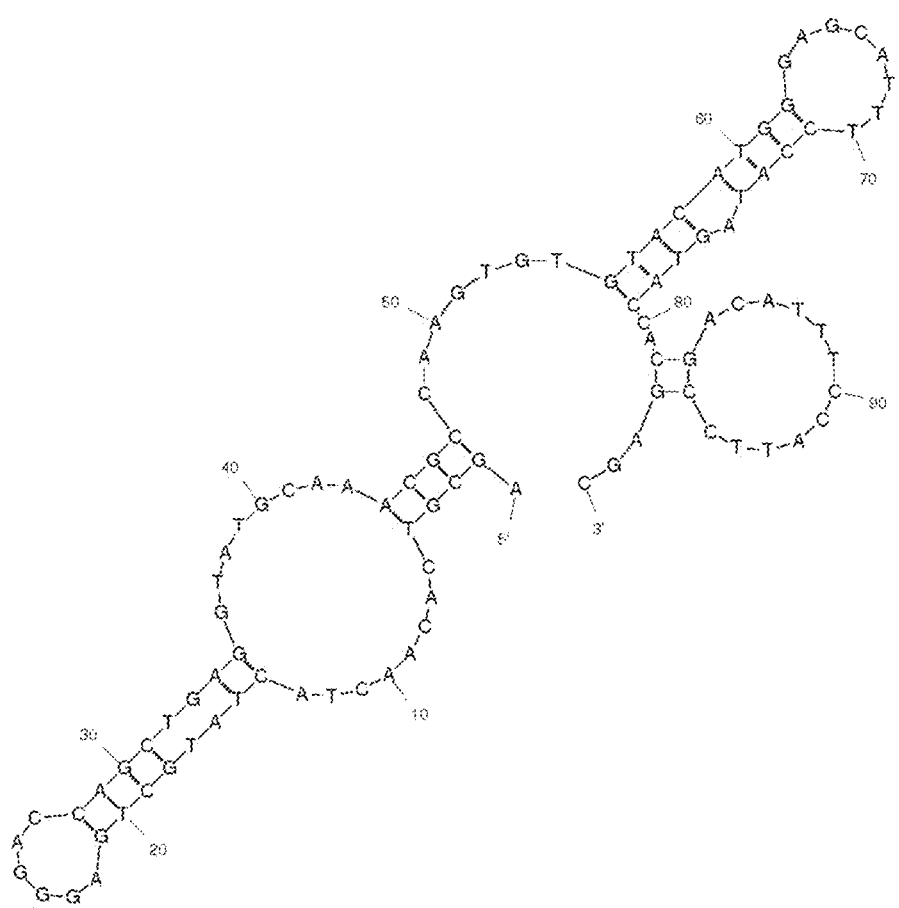
FIG. 7 is a schematic presentation of a possible structure of the sequence representative from class "CCACC" in it's different states.

FIGS. 6 and 7 depicts the results obtained from f-fold analysis. The left structure (A) is the pre-bind recongnition state. In the presence of gibberellins, the structure will switch to either the middle (B) or right form (C) (the both of which is the more stable conformation). The "CCACC" class thus had three possible structural conformation with delta G of −14.89, −14.85, and −14.01, indicating that the structures found within the sequence are more stable than that of the "TGAGG" molecules. In addition, the structures suggest a structure-switching mechanism that exists in two states. The first state is the immobilization and recognition structure whereby the aptamer sequence is hybridized to the solid support and is "ready" to bind the gibberellins. The second state (the more stable structure) is suggestive of the aptamer formation in the presence of gibberellins and the dissociation from the solid supports.

The rationale for structure-switching for class "CCACC" is derived from the change at nucleotide positions 30 to 42. This sequence space is used to hybridize with a complementary "catch" sequence that is immobilized on a solid support (magnetic beads or agarose beads). In the presence of gibberellins, the sequence refolds into a more stable structure and displaces the capture sequence, thereby releasing itself from the solid supports.

FIG. 6 depicts the structure of the sequence representative from class "TGAGG" in its most stable form and while other structures exist, the most stable structure had a delta G of −11.96 kcal/mol at 22 degrees Celsius. Although no clear structure-switching conformation is observed for class "TGAGG", the existence of hairpin structures suggests a possible motif that may recognize gibberellins.

Initial Binding Response Test

Figures 8, 9:
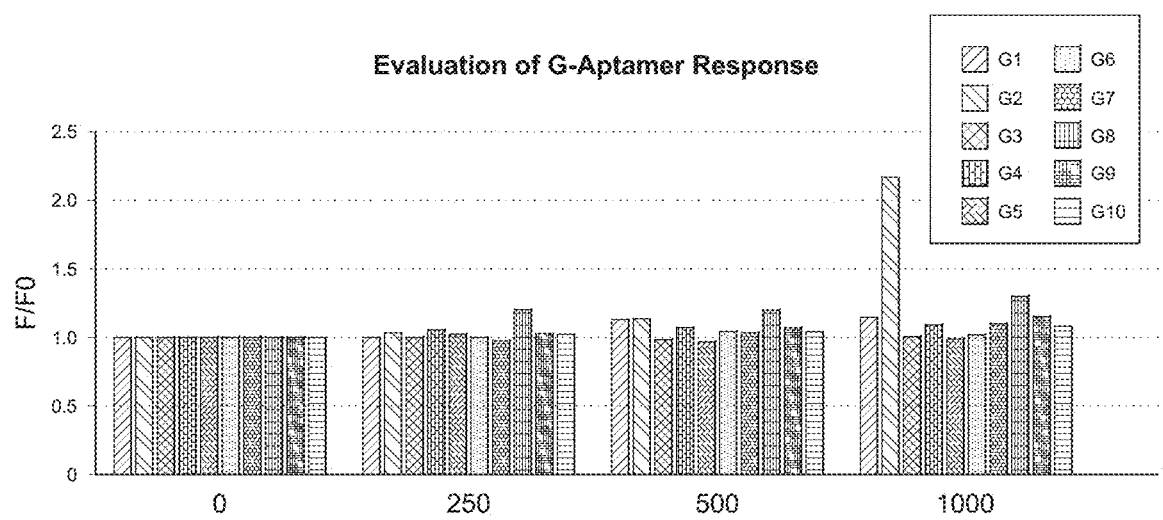
FIG. 8 is a table depicting representative sequence groups G1-G10.
FIG. 9 is a graph depicting binding response of G1 to G10 at different concentrations of gibberellins.

SEQ ID'S 1-8; 10 and 11 listed in FIG. 3 were chemically synthesized and purified using 10% denaturing polyacrylamide gel electrophoresis. The SEQ ID'S are again listed in FIG. 8 with their corresponding group number. An initial broad response test was evaluated at three different concentrations (250 uM, 500 uM, and 1000 uM). All data values were produced in at least triplicates. Overall, the sequences demonstrated some activity response against the gibberellins mixture. G2 was selected as the ideal aptamer for further investigation. FIG. 9 depicts the binding response of G1 to G10 at three different concentrations of gibberellins.

Binding of G2 Against Gibberellins

Figure 10:
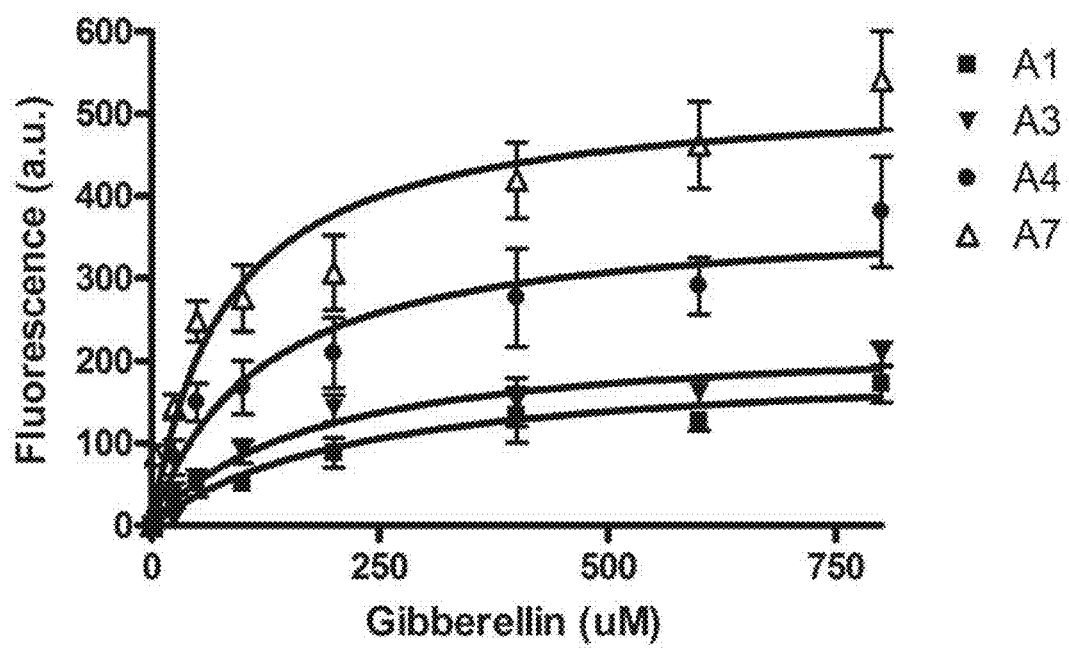
FIG. 10 is a graph depicting the combined binding response of G2 to four gibberellins.
Figure 11:
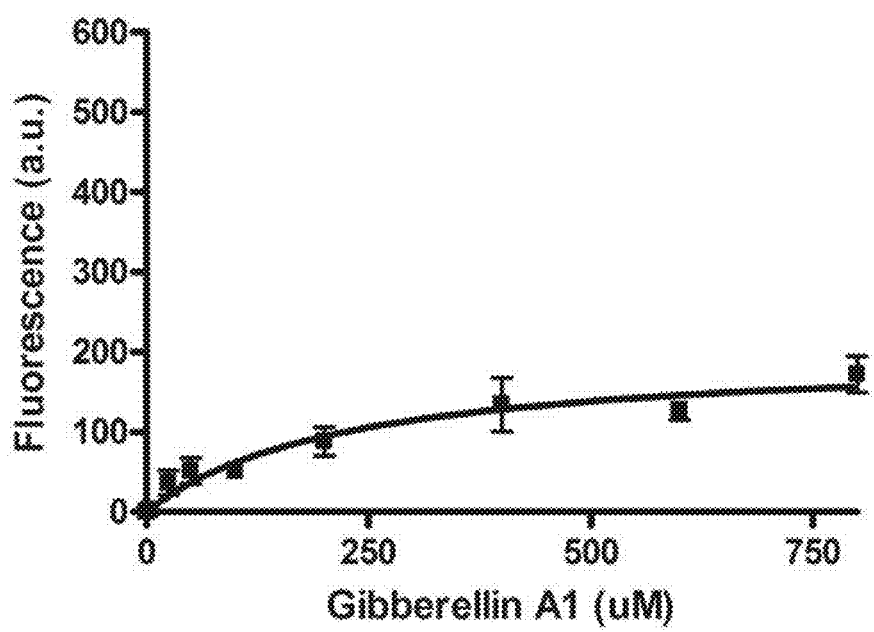
FIG. 11 is a graph depicting a response curve of G2 to gibberellin A1.
Figure 12:
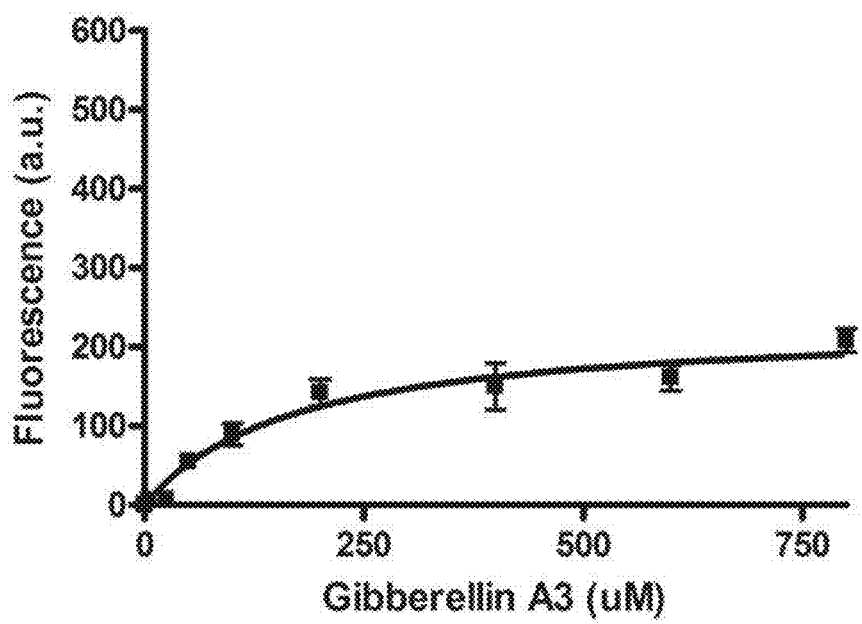
FIG. 12 is a graph depicting a response curve of G2 to gibberellin A3.
Figure 13:
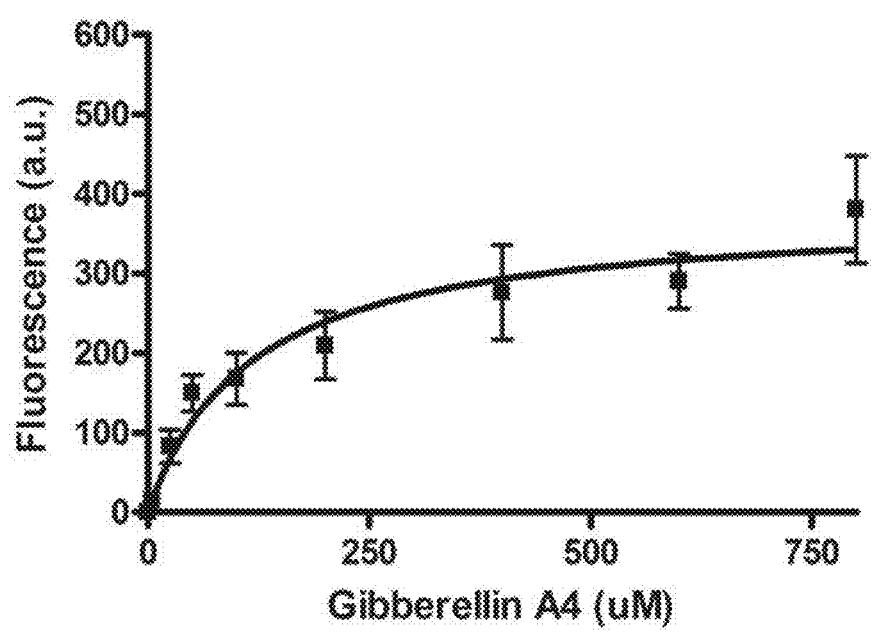
FIG. 13 is a graph depicting a response curve of G2 to gibberellin A4.
Figure 14:
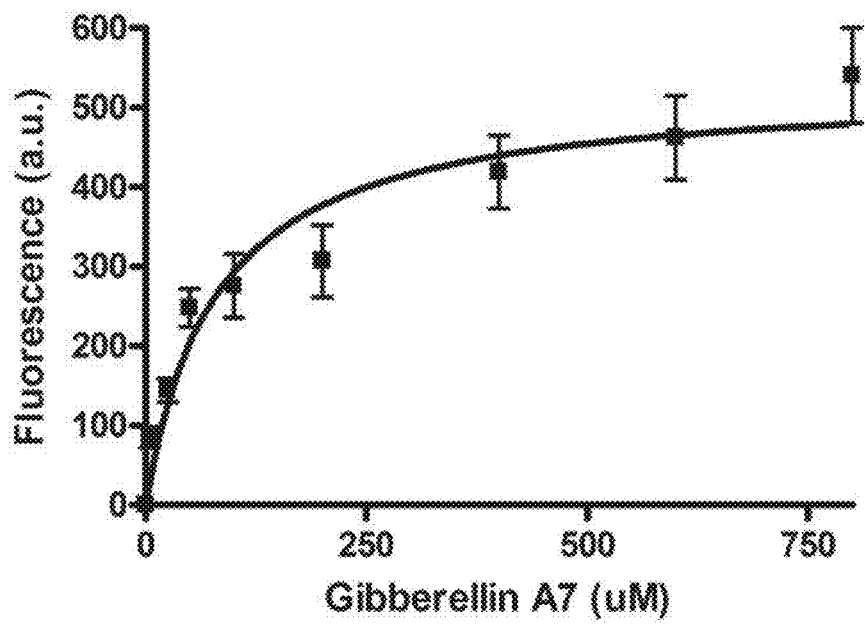
FIG. 14 is a graph depicting a response curve of G2 to gibberellin A7.

FIG. 10 depicts the combined binding response of G2 evaluated against individual gibberellins (A1, A3, A4, and A7) over concentrations ranging from 0 to 1 mM. Fluorescent measurements were based on the amount of fluorescent DNA released from the solid support.

As can be seen from FIG. 10, the G2 aptamer responded to a mixture of gibberellins. FIG. 11 to FIG. 14 shows that the G2 aptamer had the highest activity response against gibberellin A7 and the lowest activity against gibberellin A1. The approximate $K_d$ values are as follows: gibberellin A1—225 uM, gibberellin A3—171 uM, gibberellin A4—116 uM, and gibberellin A7—80 uM.

Conclusion of Aptamer Selection Process

Screening for aptamers against gibberellins $A_1$, $A_3$, $A_4$, and A7 was successfully performed over 20 cycles of in vitro selection experiments. By using all four target molecules in one pool for selection, the final aptamer G2 was able to recognize all four targets.

Embodiments

A first embodiment of a ligand binding assay may be a lateral or vertical flow assay which includes aptamers which are bound to a carrier. The carrier may be gold nanoparticles and the gold nanoparticles may be bound to the aptamer by thiolation. An indicator is provided in the form of a binding signal from saturation of aptamer binding sites on the carrier. The lateral or vertical flow assay may be an inhibition assay. At least one thiolated aptamer is bound to the gold via interactions between the lattice structure of the gold nanoparticles and thiol groups on the aptamer oligonucleotide.

The surface plasma resonance from a highly localized concentration of gold nanoparticles results in a visual indicator in the absence of gibberellins. The visual indicator may be perceivable as a visible red signal on an indication portion of the lateral or vertical flow assay. The depletion of the binding signal from saturation of aptamer binding sites on the gold nanoparticles result in the absence of the red signal in the presence of gibberellins. The visible red signal is a result of the aptamer bound gold nanoparticle complex saturating binding sites on the carrier and thus preventing the aggregation of the gold particles.

Figure 15:
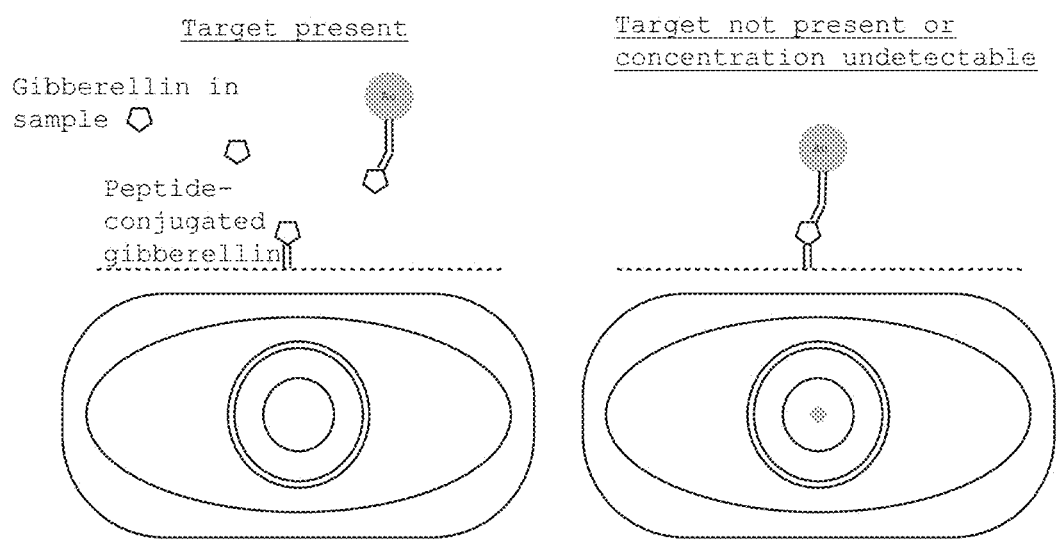
FIG. 15 is a competitive inhibition assay.

The ligand binding assay may be in the form of a lateral flow or vertical flow disposable test with the product applied to an indication portion, such as a membrane, of the disposable test. The vertical flow disposable test may be a standard sandwich vertical flow assay or a competitive vertical flow assay. The test may comprise a competitive inhibition modality wherein the negative control represents a visible red portion on the membrane of the disposable test unit. In the competitive format, should a target be present in the test specimen this will saturate the binding sites on the aptamer-coated gold nanoparticles so that the aptamer coated gold nanoparticles will no longer bind to the membrane in which an ovalbumin or other peptide-conjugated gibberellin is being used to facilitate binding to the membrane. This process is summarized in FIG. 15.

Figure 16:
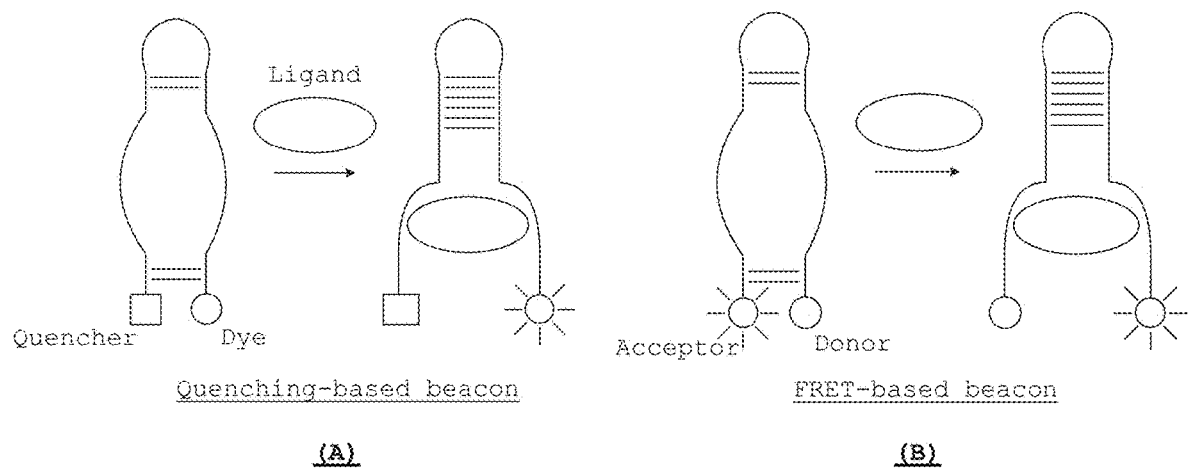
FIG. 16 is depictions of a fluorescence and a fluorescent resonance energy transfer (FRET) assay.

A second embodiment of the ligand binding assay may be in the form of a non-radioactive ligand binding assay which includes aptamers which are chemically linked to a fluorophore and quencher pair. In this embodiment, the visual indicator is provided in the form of fluorescence of the solution in the presence of gibberellins. The fluorophore and quencher pair may be a nucleic acid dye and fluorescent hybridization probe. It follows that in the presence of gibberellins, the quencher is stripped from the fluorophore/quencher pair, resulting in fluorescence signal specific to the fluorophore as indicated in FIG. 16(A). Moreover, the increase in binding signal thus reveals the presence of antigen and further the signal can be quantified against a standard.

The test 1 for the target would take place in the buffer solution used for extraction of the antigen from the source material of the specimen. The extraction buffer solution could include, but is not limited to, TBS (Tris Buffered Saline). Furthermore, a fluorimeter is used to detect fluorescence of fluorophore-specific fluorescence and potentially quantification thereof against pre-calibrated standards or values.

The ligand binding assay may include aptamers which are chemically linked to an acceptor and donor pair such that the visual indicator is provided in the form of fluorescence of the solution in the presence of gibberellins. In the presence of antigen, the acceptor is stripped from the acceptor/donor pair, resulting in a change in emission wavelength as indicated in FIG. 16(B). It should be noted that a difference in emission wavelength signal thus reveals the presence of the antigen. In view of the above, the difference between initial and endpoint emission wavelengths can be quantified against a standard and provide quantitative analysis of target concentration.

The test for the target would take place in the buffer solution used for extraction of the antigen from the source material of the specimen wherein the extraction buffer solution could include, but is not limited to, TBS (Tris Buffered Saline). Furthermore, a fluorimeter is used to detect fluorescence of fluorophore-specific fluorescence and potentially quantification thereof against pre-calibrated standards or values. Fluorescence is very sensitive and can detect very low concentrations of analyte. It is also very specific as the fluorophore signal is very specific. This produces a very high-quality signal with good signal to noise ratio as the fluorophores are designed to emit within a very narrow band gap.

It is envisaged that the invention will provide a point-of-use ligand binding assay for rapid detection of gibberellins. Specifically, the point-of-use assay will be advantageous to determine germination energy of seeds which will provide an indication of quality.

SEQUENCE LISTING

| SEQUENCE ID NO. | SEQUENCE |
|---|---|
| 1 | 5'-CCACCACAAAGCTGAGGTATGCGGGTATGCAGCTGTAACGATGCCGTTGCTGTAGGCTGCAA-'3 |
| 2 | 5'-TGAGGGACCAGCTGAGGTATGCAAACGCCAAGTGTGTACATGGGAGCATTTCCATAGTACCA-'3 |
| 3 | 5'-TGAGGGACCGGCTGAGGTATGCAAACGCCTGATAAGTAAAGTAGATCTCTACTGTGCTCATA-'3 |
| 4 | 5'-TGAGGACAACGCTGAGGTATGCAAATAACAACAATTCAGAGGCTAGGCCCTCTGAGGATCGT-'3 |
| 5 | 5'-CGACCAGGCAGCTGAGGTATGCTGTAACACATAGAATTATGGTATATGGCAGTCGATTACGA-'3 |
| 6 | 5'-GCACCCGGAAGCTGAGGTATGCCACAAGTCAGTGGCTATGACGAATCATAGCCGTGACCTCG-'3 |
| 7 | 5'-CGCCAGGCATGCTGAGGTATGCTGTAACACATGAGAGTAATGATATCGGGACAGGTACGCCC-'3 |
| 8 | 5'-CACCAAGGCAGCTGAGGTATGCTGTAACACAAGGTACAAACGACTTAAGTTTGGCCCTGACT-'3 |
| 9 | 5'-TGCCAAGCATGCTGAGGTATGCTGTAACACACTAGCCTACGGTAAGGAACGTTGTGGTTGCA-'3 |
| 10 | 5'-TGAGGAGCGAGCTGAGGTATGCCAACAACACGTGTTCAGTACGTGTACTAGAAACGCGTCGT-'3 |
| 11 | 5'-CCGGTAGGGTGCTGAGGTATGCTGTAACACACAAAAATTGCGTCTACGCAATCTCGGATGAC-'3 |
| 12 | 5'-NHMCVNNNNHDGCTGAGGTATGCNNNHWNDYDDNDNNHHHNHNVVHNNNNNDNNDBNHNNNHD-'3 |
| 13 | 5'-TGAGGDVNVNGCTGAGGTATGCMAAYDHMHNVNNNNNHNNNNNNNNNNNNNNNNNNNDHNNN-'3 |

The invention claimed is:

1. A ligand binding assay kit for detecting the presence of gibberellins in a sample comprising:
   a target binding element selected to bind to a gibberellin selected from the group consisting of $GA_1$, $GA_3$, $GA_4$, and $GA_7$; wherein
   the target binding element is associated with a visual indicator which indicates the presence of the gibberellin in the sample when the target binding element binds to the gibberellin, wherein the target binding element is an aptamer.

2. The assay kit of claim 1 wherein the aptamer has 62 nucleotides with the nucleic acid sequence:

(SEQ ID NO: 12)
   5'-NHMCVNNNHDGCTGAGGTATGCNNNHWNDYDDNDNNHHHNHNVVHNN

NNNDNNDBNHNNNHD-3', wherein Y is T or C;
   wherein M is A or C;
   wherein W is A or T
   wherein B is G or C or T;
   wherein D is A or G or T;
   wherein H is A or C or T;
   wherein V is A or G or C;
   wherein N is A or G or C or T;
   or its compliment, or an RNA equivalent of the molecule or its complement.

3. The assay kit of claim 1 wherein the aptamer has 62 nucleotides with the nucleic acid sequence (SEQ ID NO: 13)
   5'-TGAGGDVNVNGCTGAGGTATGCMAAYDHMHNVNNNNNHNNNNNNNNN

NNNNNNNNNNNDHNNN-3' wherein Y is T or C;
   wherein M is A or C;
   wherein D is A or G or T;
   wherein H is A or C or T;
   wherein V is A or G or C;
   wherein N is A or G or C or T;
   or its compliment, or an RNA equivalent of the molecule or its complement.

4. The assay kit of claim 1 wherein the aptamer comprises a nucleic acid sequence with at least 90% homology to any one of sequences SEQ ID NO 1-11.

5. The assay kit of claim 1 wherein the ligand binding assay is a lateral or vertical flow wherein the aptamers are bound to a carrier and the indicator is provided in the form of a binding signal from saturation of aptamer binding sites on the carrier.

6. The assay kit of claim 5 wherein the assay is an inhibition assay.

7. The assay kit of claim 5 wherein the carrier is a gold nano-particle bound to the aptamer by thiolation.

8. The assay kit of claim 7 wherein a surface plasma resonance from a highly localized concentration of gold nano-particles provides a visual indicator in the absence of gibberellins in the sample.

9. The assay kit of claim 8 wherein the visual indicator is perceivable as a visible red signal on an indication portion of the lateral or vertical flow assay.

10. The assay kit of claim 9 wherein the visible red signal is a result of the aptamer bound gold nano-particle complex saturating binding sites on the carrier and thus preventing the aggregation of the gold particles.

11. The assay kit claim 1 wherein the assay is a non-radioactive ligand binding assay which includes aptamers which are chemically linked to a fluorophore and quencher pair such that the visual indicator is provided in the form of fluorescence in the presence of gibberellins.

12. The assay kit of claim 11 wherein the fluorophore and quencher pair is a nucleic acid dye and fluorescent hybridization probe.

13. The assay kit of claim 1 wherein the ligand binding assay includes aptamers which are chemically linked to an acceptor and donor pair such that the visual indicator is provided in the form of fluorescence in the presence of gibberellins.

14. A ligand binding assay for detecting the presence of gibberellins in a sample comprising:
   binding an aptamer to a gibberellin selected from the group consisting of $GA_1$, $GA_3$, $GA_4$, and $GA_7$, wherein the aptamer is associated with a visual indicator which indicates the presence of the gibberellin in the sample when the aptamer binds to the gibberellin; and
   detecting the gibberellin by visualizing the visual indicator.

* * * * *

UNITED STATES PATENT AND TRADEMARK OFFICE
CERTIFICATE OF CORRECTION

PATENT NO. : 11,046,960 B2
APPLICATION NO. : 16/320934
DATED : June 29, 2021
INVENTOR(S) : Charles Stephen Whitehead et al.

It is certified that error appears in the above-identified patent and that said Letters Patent is hereby corrected as shown below:

On the Title Page

On Page 2, Column 2, Item (56), Line 12, under Other Publications, delete "pIntphys" and insert --plntphys--.

On Page 2, Column 2, Item (56), Line 13, under Other Publications, delete ""Simul taneous" and insert --"Simultaneous--.

In the Specification

In Column 2, Line 13, delete "T" and insert --T;--.

In Column 6, Line 65, delete "2)" and insert --2--.

In Column 7, Line 1, delete "6100)." and insert --6100.--.

In Column 7, Line 28, delete "recongnition" and insert --recognition--.

In Column 8, Line 14, delete "A7" and insert --$A_7$--.

In the Claims

In Column 17, Line 22 (Claim 2), delete "T" and insert --T;--.

In Column 18, Line 23 (Claim 11), delete "claim" and insert --of claim--.

Signed and Sealed this
Twenty-fourth Day of October, 2023

Katherine Kelly Vidal
*Director of the United States Patent and Trademark Office*

SEQUENCE LISTING

<160> NUMBER OF SEQ ID NOS: 13

<210> SEQ ID NO 1
<211> LENGTH: 62
<212> TYPE: DNA
<213> ORGANISM: Artificial Sequence
<220> FEATURE:
<223> OTHER INFORMATION: Synthetic

<400> SEQUENCE: 1
ccaccacaaa gctgaggtat gcgggtatgc agctgtaacg atgccgttgc tgtaggctgc    60
aa                                                                   62

<210> SEQ ID NO 2
<211> LENGTH: 62
<212> TYPE: DNA

<213> ORGANISM: Artificial Sequence
<220> FEATURE:
<223> OTHER INFORMATION: Synthetic

<400> SEQUENCE: 2
tgagggacca gctgaggtat gcaaacgcca agtgtgtaca tgggagcatt tccatagtac   60
ca                                                                 62

<210> SEQ ID NO 3
<211> LENGTH: 62
<212> TYPE: DNA
<213> ORGANISM: Artificial Sequence
<220> FEATURE:
<223> OTHER INFORMATION: Synthetic

<400> SEQUENCE: 3
tgagggaccg gctgaggtat gcaaacgcct gataagtaaa gtagatctct actgtgctca   60
ta                                                                 62

<210> SEQ ID NO 4
<211> LENGTH: 62
<212> TYPE: DNA
<213> ORGANISM: Artificial Sequence
<220> FEATURE:
<223> OTHER INFORMATION: Synthetic

<400> SEQUENCE: 4
tgaggacaac gctgaggtat gcaaataaca acaattcaga ggctaggccc tctgaggatc   60
gt                                                                 62

<210> SEQ ID NO 5
<211> LENGTH: 62
<212> TYPE: DNA
<213> ORGANISM: Artificial Sequence
<220> FEATURE:
<223> OTHER INFORMATION: Synthetic

<400> SEQUENCE: 5
cgaccaggca gctgaggtat gctgtaacac atagaattat ggtatatggc agtcgattac   60
ga                                                                 62

<210> SEQ ID NO 6
<211> LENGTH: 62
<212> TYPE: DNA
<213> ORGANISM: Artificial Sequence
<220> FEATURE:
<223> OTHER INFORMATION: Synthetic

<400> SEQUENCE: 6
gcacccggaa gctgaggtat gccacaagtc agtggctatg acgaatcata gccgtgacct   60
cg                                                                 62

<210> SEQ ID NO 7
<211> LENGTH: 62
<212> TYPE: DNA
<213> ORGANISM: Artificial Sequence
<220> FEATURE:
<223> OTHER INFORMATION: Synthetic

<400> SEQUENCE: 7
cgccaggcat gctgaggtat gctgtaacac atgagagtaa tgatatcggg acaggtacgc   60
cc                                                                 62

<210> SEQ ID NO 8
<211> LENGTH: 62
<212> TYPE: DNA
<213> ORGANISM: Artificial Sequence
<220> FEATURE:
<223> OTHER INFORMATION: Synthetic

<400> SEQUENCE: 8
caccaaggca gctgaggtat gctgtaacac aaggtacaaa cgacttaagt ttggccctga    60
ct    62

<210> SEQ ID NO 9
<211> LENGTH: 62
<212> TYPE: DNA
<213> ORGANISM: Artificial Sequence
<220> FEATURE:
<223> OTHER INFORMATION: Synthetic

<400> SEQUENCE: 9
tgccaagcat gctgaggtat gctgtaacac actagcctac ggtaaggaac gttgtggttg    60
ca    62

<210> SEQ ID NO 10
<211> LENGTH: 62
<212> TYPE: DNA
<213> ORGANISM: Artificial Sequence
<220> FEATURE:
<223> OTHER INFORMATION: Synthetic

<400> SEQUENCE: 10
tgaggagcga gctgaggtat gccaacaaca cgtgttcagt acgtgtacta gaaacgcgtc    60
gt    62

<210> SEQ ID NO 11
<211> LENGTH: 62
<212> TYPE: DNA
<213> ORGANISM: Artificial Sequence
<220> FEATURE:
<223> OTHER INFORMATION: Synthetic

<400> SEQUENCE: 11
ccggtagggt gctgaggtat gctgtaacac acaaaaattg cgtctacgca atctcggatg    60
ac    62

<210> SEQ ID NO 12
<211> LENGTH: 62
<212> TYPE: DNA
<213> ORGANISM: Artificial Sequence
<220> FEATURE:
<223> OTHER INFORMATION: Synthetic
<220> FEATURE:
<221> NAME/KEY: Misc_feature
<222> LOCATION: (1)...(1)
<223> OTHER INFORMATION: n = a, g, t, c
<220> FEATURE:
<221> NAME/KEY: Misc_feature
<222> LOCATION: (6)...(8)
<223> OTHER INFORMATION: n = a, g, t, c
<220> FEATURE:
<221> NAME/KEY: Misc_feature
<222> LOCATION: (23)...(25)
<223> OTHER INFORMATION: n = a, g, t, c
<220> FEATURE:
<221> NAME/KEY: Misc_feature
<222> LOCATION: (28)...(28)

```
<223> OTHER INFORMATION: n = a, g, t, c
<220> FEATURE:
<221> NAME/KEY: Misc_feature
<222> LOCATION: (33)...(33)
<223> OTHER INFORMATION: n = a, g, t, c
<220> FEATURE:
<221> NAME/KEY: Misc_feature
<222> LOCATION: (35)...(36)
<223> OTHER INFORMATION: n = a, g, t, c
<220> FEATURE:
<221> NAME/KEY: Misc_feature
<222> LOCATION: (40)...(40)
<223> OTHER INFORMATION: n = a, g, t, c
<220> FEATURE:
<221> NAME/KEY: Misc_feature
<222> LOCATION: (42)...(42)
<223> OTHER INFORMATION: n = a, g, t, c
<220> FEATURE:
<221> NAME/KEY: Misc_feature
<222> LOCATION: (46)...(50)
<223> OTHER INFORMATION: n = a, g, t, c
<220> FEATURE:
<221> NAME/KEY: Misc_feature
<222> LOCATION: (52)...(53)
<223> OTHER INFORMATION: n = a, g, t, c
<220> FEATURE:
<221> NAME/KEY: Misc_feature
<222> LOCATION: (56)...(56)
<223> OTHER INFORMATION: n = a, g, t, c
<220> FEATURE:
<221> NAME/KEY: Misc_feature
<222> LOCATION: (58)...(60)
<223> OTHER INFORMATION: n = a, g, t, c

<400> SEQUENCE: 12
nhmcvnnnhd gctgaggtat gcnnnhwndy ddndnnhhhn hnvvhnnnnn dnndbnhnnn    60 hd                                                                  62

<210> SEQ ID NO 13
<211> LENGTH: 62
<212> TYPE: DNA
<213> ORGANISM: Artificial Sequence
<220> FEATURE:
<223> OTHER INFORMATION: Synthetic
<220> FEATURE:
<221> NAME/KEY: Misc_Features
<222> LOCATION: (8)...(8)
<223> OTHER INFORMATION: n = a, g, t, c
<220> FEATURE:
<221> NAME/KEY: Misc_feature
<222> LOCATION: (10)...(10)
<223> OTHER INFORMATION: n = a, g, t, c
<220> FEATURE:
<221> NAME/KEY: Misc_feature
<222> LOCATION: (31)...(31)
<223> OTHER INFORMATION: n = a, g, t, c
<220> FEATURE:
<221> NAME/KEY: Misc_feature
<222> LOCATION: (33)...(37)
<223> OTHER INFORMATION: n = a, g, t, c
<220> FEATURE:
<221> NAME/KEY: Misc_feature
<222> LOCATION: (39)...(57)
<223> OTHER INFORMATION: n = a, g, t, c
<220> FEATURE:
<221> NAME/KEY: Misc_feature
<222> LOCATION: (60)...(62)
<223> OTHER INFORMATION: n = a, g, t, c

<400> SEQUENCE: 13
tgaggdvnvn gctgaggtat gcmaaydhmh nvnnnnnhnn nnnnnnnnnn nnnnnnndhn    60 nn                                                                  62
```